United States Patent
Hagting et al.

(10) Patent No.: US 7,659,325 B2
(45) Date of Patent: Feb. 9, 2010

(54) FUNCTIONALIZED DYES AND USE THEREOF IN OPHTHALMIC LENS MATERIAL

(75) Inventors: Joke Geesje Hagting, Groningen (NL); Theodorus Adrianus Cornelius Flipsen, Groningen (NL); Miriam Adrienne Lambertina Verbruggen, Zwolle (NL); Hendrik Smit, Harkstede (NL)

(73) Assignee: Ophtec B.V., Groningen (NL)

( * ) Notice: Subject to any disclaimer, the term of this patent is extended or adjusted under 35 U.S.C. 154(b) by 551 days.

(21) Appl. No.: 11/266,598

(22) Filed: Nov. 3, 2005

(65) Prior Publication Data

US 2007/0100018 A1     May 3, 2007

(51) Int. Cl.
  *G02B 1/04*   (2006.01)
  *C08F 8/30*   (2006.01)
  *C08K 5/23*   (2006.01)

(52) U.S. Cl. .................. 523/106; 523/107; 525/376; 524/190

(58) Field of Classification Search ............. 523/106, 523/107; 525/376
  See application file for complete search history.

(56) References Cited

U.S. PATENT DOCUMENTS

| | | | |
|---|---|---|---|
| 3,049,532 A * | 8/1962 | Gaetani ............. 534/834 |
| 3,236,645 A * | 2/1966 | Husek et al. ......... 430/243 |
| 3,658,675 A * | 4/1972 | Jones et al. .......... 430/32 |
| 4,120,570 A | 10/1978 | Gaylord |
| 4,304,895 A | 12/1981 | Loshaek |
| 4,528,311 A | 7/1985 | Beard et al. |
| 5,186,865 A * | 2/1993 | Wu et al. ............ 252/582 |
| 5,374,663 A | 12/1994 | Daicho et al. |
| 5,444,106 A | 8/1995 | Zhou et al. |
| 5,470,932 A | 11/1995 | Jinkerson |
| 5,528,322 A | 6/1996 | Jinkerson |
| 5,543,504 A | 8/1996 | Jinkerson |
| 5,623,062 A * | 4/1997 | Sasaki et al. ........ 534/653 |
| 5,662,707 A * | 9/1997 | Jinkerson ........... 623/6.17 |
| 5,712,376 A * | 1/1998 | Ruhlmann et al. ..... 534/634 |
| 6,222,023 B1 * | 4/2001 | Toishi et al. ........ 534/634 |
| 6,277,940 B1 | 8/2001 | Niwa et al. |
| 6,310,215 B1 | 10/2001 | Iwamoto |
| 6,326,448 B1 | 12/2001 | Ojio et al. |
| 6,551,529 B2 * | 4/2003 | Taguchi et al. ....... 252/585 |
| 2004/0013337 A1 | 1/2004 | Purchase et al. |
| 2006/0252844 A1 | 11/2006 | Mentak |

FOREIGN PATENT DOCUMENTS

| | | |
|---|---|---|
| EP | 0 799 864 A1 | 4/1997 |
| EP | 1 293 541 A2 | 9/2002 |
| JP | 1-280464 | 11/1989 |
| JP | 1-299560 | 12/1989 |
| JP | 10-195324 | 7/1998 |
| JP | 2007071973 A * | 3/2007 |
| WO | WO 96/31792 | 10/1996 |
| WO | WO 2005/066694 | 7/2005 |

* cited by examiner

*Primary Examiner*—Tae H Yoon
(74) *Attorney, Agent, or Firm*—Lucas & Mercanti, LLP

(57) ABSTRACT

The invention relates to transparent polymer material containing a dye which absorbs light above 400 nm. It furthermore relates to methods for producing the polymer material and a lens comprising the polymer material. In particular, the invention relates to an intraocular lens (IOL) suitable for implantation in mammals, which IOL has visible light transmission properties comparable to those of the human crystalline lens. Provided is a transparent polymer material containing at least one covalently attached dye, said dye having the general formula I:

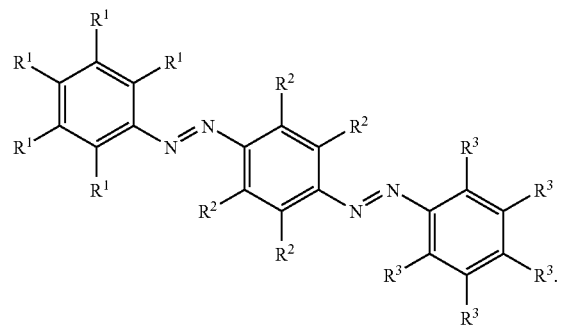

24 Claims, 2 Drawing Sheets

FUNCTIONALIZED DYES AND USE THEREOF IN OPHTHALMIC LENS MATERIAL

Figure 1:
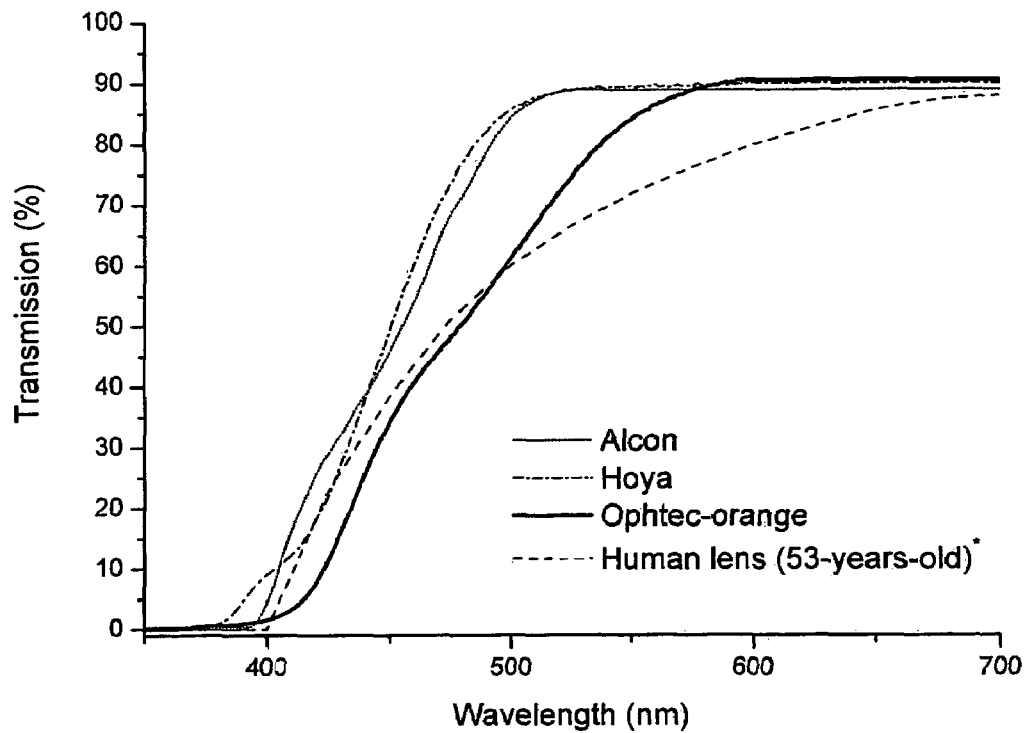

The invention relates to transparent polymer material containing a dye which absorbs light above 400 nm. It furthermore relates to methods for producing the polymer material and a lens comprising the polymer material. In particular, the invention relates to an intraocular lens (IOL) suitable for implantation in mammals, which IOL has visible light transmission properties comparable to those of the human crystalline lens.

In healthy adults the retina is generally protected from the most severe forms of light-induced damage by the outer eye structures including the cornea and crystalline lens. The cornea is a transparent proteinaceous ocular tissue located before the iris and is the only eye structure exposed directly to the environment. It is important for protecting the delicate internal structures from damage and facilitates the transmission of light through the aqueous media to the crystalline lens. The cornea is the primary light filter and therefore is particularly susceptible to excessive light exposure-related damage including corneo-conjunctival diseases such as pterygium, droplet climatic keratopathy, and pinguecula. In the healthy eye the cornea, in conjunction with the aqueous medium, absorbs, or blocks, wavelengths in the short ultraviolet UV-B and UV-C region (less than 320 nm).

The crystalline lens is an accommodating biological lens lying directly behind the iris and cornea and facilitates the convergence of both far and near images onto the retina. The natural crystalline lens blocks near UV radiation (UT-A) (320 to 400 nm) from reaching the retina. Therefore, most of the damaging UV A, B and C radiation are prevented from reaching the retina in healthy people with an intact crystalline lens and cornea. Thus in the normal mammalian eye only wavelengths between 400 and 1400 nm can reach the retina. However, high transmittance levels of violet-to-blue light (wavelengths from about 400 to about 515 nm) has been linked to retinal damage, macular degeneration, retinitis pigmentosa, and night blindness. In addition, blue light tends to be scattered in the atmosphere, especially in haze, fog, rain, and snow, which in part can cause glare, and diminished visual acuity. As the eye ages, the crystalline lens begins to take on a yellow tint that does not adversely affect visual acuity but does absorb the majority of near UV radiation. By age 54, the human lens will not transmit light below 400 nm and the transmission of light between 400 and 515 nm is greatly diminished. Thus, the natural crystalline lens protects the eye's delicate retina from near UV light throughout life and subtly yellows to orange-brown with age, increasing the amount of shorter wavelength blue light that is absorbed.

The natural crystalline lens is also susceptible to age-related degenerative eye diseases such as cataract and indirectly age-related macular disease (AMD). Cataract is a major cause of visual impairment and blindness worldwide. Cataract is a clouding of the crystalline lens caused by the coagulation of lens proteins within the capsular sac. Laboratory studies have implicated UV radiation as a cause of cataract. Furthermore, epidemiological studies have shown that certain types of cataract are associated with a history of higher ocular exposure to UV and especially WV-B radiation.

Cataracts develop slowly in most people and eventually reach the point where vision is substantially impaired resulting in near to total blindness. In these persons lens removal and replacement with synthetic polymer IOLs is the preferred means for restoring normal sight. However, once the natural crystalline lens is removed, the retina is left unprotected from damaging UV and short wavelength blue light. Early synthetic IOLs were provided with UV absorbing compounds such as benzophenone and benzotriazole-based UV light absorbers which block radiation up to about 400 nm. IOLs provided with TV absorbing compounds soon became common-place and are found in virtually all IOLs. Moreover, benzophenones and benzotriazoles can be made polymerizable and can thus be stably integrated into most modern IOL compositions including, but not limited to (meth)acrylates, silicones, and polyurethanes.

Recently, blue light absorbing dyes have been incorporated into IOL materials in order to approximate the blue light blocking effects of the aging adult natural crystalline lens. A number of IOL manufacturers have designed lenses that contain yellow dyes at concentrations that absorb, or block visible light in the blue region.

For example, U.S. Pat. No. 5,374,663 of Hoya Corporation discloses non-covalently linked yellow dyes including Solvent Yellow numbers 16, 29 and others incorporated into a polymethylmethacrylate (PMMA) polymer matrix. Moreover, Hoya also owns U.S. Pat. No. 6,310,215 that discloses acrylic-functionalized pyrazolone dyes suitable for use in acrylic and silicone IOLs. U.S. Pat. Nos. 5,470,932, 5,528, 322; 5,543,504; and 5,662,707 in the name of Alcon disclose acrylic-functionalized yellow azo dyes having an inert chemical spacer between the dye and acrylic portions of the molecule. Because the dye is acrylic-functionalized, it is polymerizable with the lens polymer and thus stably incorporated into the IOL polymer matrix. Similarly, U.S. Pat. No. 6,277, 940 and U.S. Pat. No. 6,326,448 in the name of Menicon describe specific acrylic-modified azo dyes structurally similar to Alcon's. IOLs with blue light filtering capability are marketed by Alcon under the tradename AcrySof® Natural.

JP10195324 in the name of Hoya Corporation relates to the manufacture of a soft yellow intraocular lens for correcting blue blindness by using a copolymer obtained by polymerizing a mixture obtained by mixing a yellow reactive dye with n-butyl acrylate, phenylethyl methacrylate, a fluorine compound, a ultraviolet absorber and a cross-linking in the presence of a polymerization initiator.

EP1293541 of Canon-Staar Co. discloses two types of yellow dyes capable of chemical bonding to a silicone, which is a material for an intraocular lens. The dyes have a maximum absorbance of about 350-450 nm. The first type of the Canon-Staar dye is an azo-pyrozolone compound which is based on Solvent Yellow 16. The second type has a phenylazophenyl core structure which is functionalized by N-linked allyl groups to allow for covalent attachment to silicone material. The transmission spectra of polymers containing exemplary yellow dyes disclosed in EP1293541, optionally in combination with a conventional UV absorber, show that the material is capable of blocking light up to about 380 nm, after which the transmission curve fairly steeply increases to 90% transmission at about 500 nm.

Whereas the known second generation "blue-light-blocking" IOLs show improved absorption characteristics as compared to the first generation of UV-absorbing IOLs, the transmission properties of current yellow IOLs are still not comparable to those of the aged human crystalline lens. The specific filtering of violet and blue light by the yellow dye is not physiological and results, among others, in reduced vision at dusk. Also during daylight, a yellow filter is inferior to the light filtering properties of a physiological lens. Importantly, the transmission of known blue-light-blocking yellow IOLs at 500 nm is typically around 90-95% and none of them displays the softly rounded transmission curve of an aged human lens with a transmission of about 40% at 450 nm and only about 60% at 500 nm. As will be understood, any deviation in an IOL from the natural transmission spectrum has adverse effects on colour perception by and overall comfort of the operated patient.

Therefore, it is an object of the present invention to provide a polymer material which is suitably used in an ophthalmic lens, such as an IOL, and which more closely imitates the softly rounded transmission curve above 400 nm of an aged human lens as compared to existing optical polymers. In particular, it is an object to provide an IOL which fully blocks rays op to and including 400 nm and displays 70% or less transmission of the blue light at 500 nm.

These objects were met by the provision of a transparent polymer material containing at least one covalently bound bis-azo dye of the general formula (I):

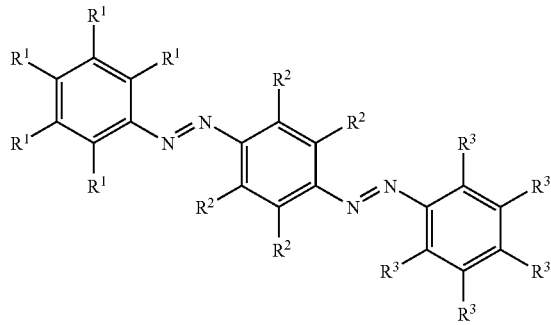

Formula I wherein each of $R^1$ is independently selected from hydrogen, sulfonate, nitro, halogen, nitril, phenyl, carboxylate, —(CH$_2$)$_n$—X$^1$—H and —X$^2$—(CH$_2$)$_n$—CH$_3$, wherein X$^1$ is O, NH, CH$_2$ or S; X$^2$ is O, NH, S, S(=O)$_2$, C(=O)O; and n is an integer in the range 0 to 20.

each of $R^2$ is independently selected from hydrogen, sulfonate, nitro, halogen, nitril, phenyl, carboxylate, —(CH$_2$)$_n$—X$^1$—H and —X$^2$—(CH$_2$)$_n$—CH$_3$, wherein X$^1$ is O, NH, CH$_2$ or S; X$^2$ is O, NH, S, S(=O)$_2$, C(=O)O; and n is an integer in the range 0 to 20; or wherein two $R^2$ groups together with the C-atoms to which they are bound form a benzene ring;

each of $R^3$ is independently selected from hydrogen, sulfonate, nitro, halogen, nitril, phenyl, carboxylate, —(CH$_2$)$_n$—X$^1$—H and —X$^2$—(CH$_2$)$_n$—CH$_3$, wherein X$^1$ is O, NH, CH$_2$ or S; X$^2$ is O, NH, S, S(=O)$_2$, C(=O)O; and n is an integer in the range 0 to 20, provided that at least one $R^3$ is a linker moiety L through which the dye is covalently bound to the polymer.

The aliphatic moieties of the substituents can be branched or linear.

It was found that a "bisazo" (also referred to as "disazo" or "di-azo") dye of formula I is particularly suitable for the manufacture of transparent polymer material having visible light transmission properties essentially identical to those reported for an aged human crystalline lens. FIG. 1 shows the transmission spectrum of a transparent polymer of the invention containing a bisazo dye of Formula I ("Ophtec-orange") and a conventional UV-absorbing compound. The polymer has an orange to orange-brown appearance. Also shown are the spectra of two known yellow "blue-light absorbing" IOLs (AcrySof Natural IOL from Alcon and Hoya IOL (HOYA YA-60BB) and the reported transmission spectrum of an aged human lens (Boethner. E. A. and Wolter. J. R., "Transmission of the Ocular Media", Investigative Ophthalmology, Vol. 776-783, 1962). Clearly, the polymer material of the invention more closely imitates the softly rounded transmission curve above 400 nm of an aged human lens; it efficiently blocks rays up to about 400-410 nm and transmission at 450 and 500 nm is approximately 35% and 60%, respectively. In contrast, the Alcon and Hoya materials transmit approximately 50% of the light at 450 nm and nearly 90% at 500 nm.

Without wishing to be bound by theory, it is believed that the extended conjugated system of the (substituted) phenylazophenylazophenyl structure depicted in Formula I is responsible for the softly rounded transmission curve above 400 nm and the relatively low transmission in the 450-550 nm region, which is not observed for the heretofore known blue light blocking IOLs. The phenyl carrying the $R^1$ groups will herein be referred to as the "first phenyl ring", the phenyl carrying the $R^2$ groups will be referred to as the "second phenyl ring" and the phenyl carrying the $R^3$ groups will herein be referred to as the "third phenyl ring".

Whereas either one or all three phenyl rings can be fully substituted, it is preferred that at least three, more preferably four $R^1$ groups are hydrogen. Likewise, preferably at least two $R^2$ groups are hydrogen and/or at least two $R^3$ groups are hydrogen. Preferred positions for $R^1$ and $R^3$ substituents other than hydrogen are the para-position on the first phenyl ring and the meta- and para-positions on the third phenyl ring. As used herein, any position of a substituent on a phenyl ring (ortho-, meta- or para-) is made with reference to the azogroup connecting the ring to its neighbouring phenyl ring.

According to the invention, the at least one blue-light absorbing bisazo dye of Formula I is chemically bound to the polymer material to ensure that the polymer is colourfast and the dye is non-extractable (i.e. will not bleed or leach out of the polymer material). It is to be understood that the dye is present essentially throughout the transparent material, and not as a layer or coating which is applied onto existing polymer material. Especially if the polymer material of the invention is to be used for the manufacture of an ophthalmic lens, like an IOL, or other object to be inserted in the body, it is important that the dye does not leak out of the polymer matrix after it is inserted in the body.

Preferably, the dye is covalently bound by one linker moiety L to the transparent polymer. A preferred position of the linker moiety is the para-position. Suitable linker moieties for the covalent attachment of dyes to optical polymers are known in the art. See for example the teaching of EP1293541. Also suitable are the polymerizable acrylate/methacrylate groups comprising a spacer moiety for attachment to the polymer as disclosed in U.S. Pat. No. 5,470,932. In one embodiment, a linker moiety is selected from the group consisting of —(CH$_2$)$_a$—CH$_2$—CH$_2$—; —(CH$_2$)$_b$—Z$^1$—(CH$_2$)$_a$—CH$_2$—CH$_2$—; —(CH$_2$)$_b$—C(=O)—Z$^1$—(CH$_2$)$_a$—CH(R$^5$)—CH$_2$—; —(CH$_2$)$_b$—Z$^1$—C(=O)—(CH$_2$)$_a$—CH(R$^5$)—CH$_2$—; —Z$^2$—(CH$_2$)$_c$—Z$^1$—(CH$_2$)$_a$—CH(R$^5$)—CH$_2$—; —Z$^2$—(CH$_2$)$_c$—C(=O)—Z$^1$—(CH$_2$)$_a$—CH(R$^5$)—CH$_2$— and —Z$^2$—(CH$_2$)$_c$—Z$^1$—C(=O)—(CH$_2$)$_a$—CH(R$^5$)—CH$_2$—; wherein a and b are independently an integer from 0 to 10 and wherein c is an integer from 1 to 10; wherein $Z^1$ and $Z^2$ are independently —O— or —NR$^6$—; and wherein $R^5$ and $R^6$ are independently hydrogen, or linear or branched alkyl of C$_1$-C$_{10}$.

In one embodiment, b is 0. Preferably, $Z^1$ is oxygen. For example, the dye is covalently bound to the polymer by —O—CH$_2$—CH$_2$—; —NH—CH$_2$—CH$_2$—; —O—C(=O)—CH(CH$_3$)—CH$_2$—; —O—C(=O)—CH$_2$—CH$_2$—, —O—CH$_2$—CH$_2$—O—C(=O)—CH(CH$_3$)—

CH$_2$— or —O—CH$_2$—CH$_2$—O—CH$_2$—CH$_2$—, wherein the oxygen or nitrogen is attached to the dye, preferably at the para-position, and wherein the CH$_2$ is attached to the polymer.

In one embodiment, at least one R$^3$ at the meta-position is a linear or branched C$_1$-C$_{10}$ alkyl, preferably a C$_1$-C$_4$ alkyl, more preferably a methylene. For example, the dye has the general formula II:

Formula II

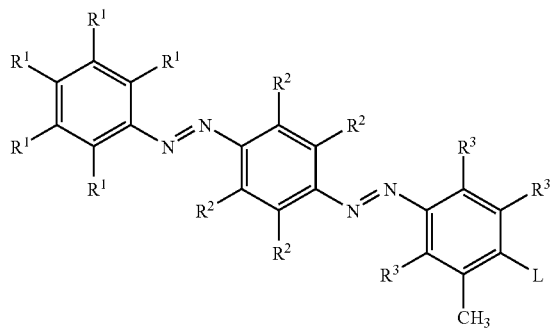

wherein
each of R$^1$, R$^2$ and R$^3$ is independently selected from hydrogen, sulfonate, nitro, halogen, nitril, phenyl, carboxylate, —(CH$_2$)$_n$—X$^1$—H and —X$^2$—(CH$_2$)$_n$—CH$_3$, wherein X$^1$ is O, NH, CH$_2$ or S; X$^2$ is O, NH, S, S(=O)$_2$, C(=O)O; and n is an integer in the range 0 to 20; or wherein two R$^2$ groups together with the C-atoms to which they are bound form a benzene ring; and wherein L is a liner moiety through which the dye is covalently bound to the polymer.

In a specific aspect, the dye is of the formula II wherein R$^1$, R$^2$ and R$^3$ are hydrogen. Such a dye is readily prepared from the dye 4-[[p-(phenylazo)phenyl]azo]-o-cresol, which is commercially available under the name Disperse Yellow 7. The hydroxyl group on the third phenyl ring is advantageously used to provide the dye with a linker moiety (see further below), for example the dye can be functionalized with an O-linked allyl or O-linked (meth)acryloyl according to methods known in the art.

In another aspect of the invention, R$^1$ at the para-position is a sulfonate and wherein at least one R$^3$ at the meta-position is a carboxylate. The terms "sulfonate" and "carboxylate" as used herein are meant to include both the acid and salts (e.g. sodium) of the respective substituents. Preferably, a linker moiety at the para-position chemically links the dye to the polymer.

For example, the dye is of the formula III:

Formula III

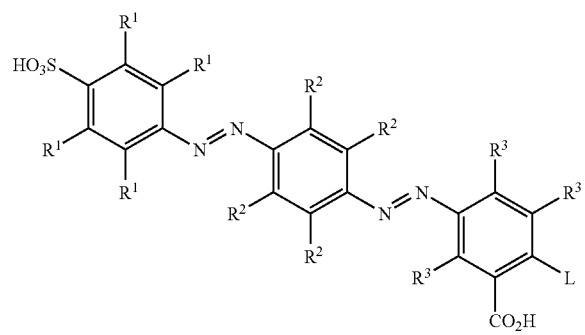

The R$^1$, R$^2$ and R$^3$ groups of Formula III are as defined for Formula II herein above. Preferably, the R$^3$ at the meta-position is a linear or branched C$_1$-C$_{10}$ alkyl substituent. Preferably, the alkyl is a C$_1$-C$_4$ alkyl, more preferably, R$^3$ is CH$_3$. In a specific aspect, the dye is of the formula III wherein all of R$^1$ and R$^2$ and at least two of R$^3$ are hydrogen. Dyes of Formula III can be prepared by coupling diazotized 4-(4-amino-phenylazo)benzene sulfonic acid to a suitable acid, e.g. 2,3-cresotic acid or salicylic acid. Exemplary dyes include those based on the commercially available dyes Mordant Orange 10 and Mordant Orange 6.

In yet another aspect, the dye is a bisazo dye in which the second phenyl ring is substituted by two R$^2$ groups which, together with the C-atoms of the phenyl ring to which they are bound, form a benzene ring. Thus, together with the second phenyl ring the R$^2$ groups form a naphthalene. An example of such a dye is represented by Formula IV, wherein R$^1$, R$^2$ and R$^3$ are as defined above for Formula II.

Formula IV

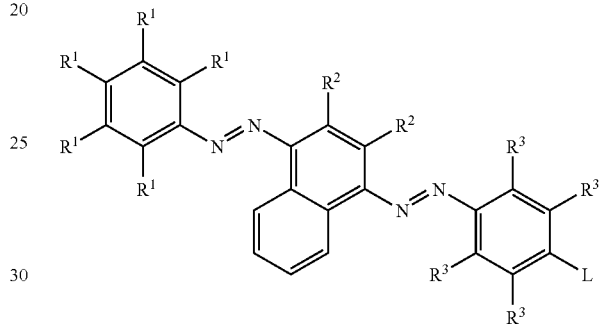

In a preferred embodiment, each of R$^1$, R$^2$ and R$^3$ of Formula IV is independently hydrogen or C$_1$-C$_4$ alkyl. Dyes of Formula IV can be prepared by coupling diazotized aniline to 1-naphtylamine, then isolating the product, diazotizing and coupling to phenol The phenol group can be used to attach a linker moiety. Exemplary dyes include those based on the commercially available dye Disperse Orange 13, also known under the name Solvent Orange 52.

As will be understood, the dyes of Formula's II, III and IV represent specific examples of dyes of general Formula I. The total amount of the dye of general formula I in a transparent polymer material can vary according to the desired application of the material. Typically, it is less than 10 parts by weight (10 wt %) with respect to 100 parts by weight of the monomers making up the polymer material. Preferably, it is less than 5 wt %. For use in ophthalmic lenses such as IOLs, it is generally less than about 1 wt %, preferably less than about 0.1 wt %, more preferably less than 0.025 wt %.

In addition to one or more dyes of the general Formula I, a transparent polymer of the invention may contain one or more additional dyes capable of absorbing light within the visible light spectrum. Together with a dye of the invention, the combination of dyes may provide the polymer with a desired transmission characteristic. Exemplary yellow dyes include, without limitation, those mentioned in patent U.S. Pat. No. 5,470,932, patent applications EP 0799864, EP 1293541 and WO2005/066694.

An ultraviolet (UV) absorbing compound can also be included in the polymeric material of this invention. The UV absorbing material can be any compound which absorbs UV light, i.e., light having a wavelength shorter than about 400 nm, but does not absorb any substantial amount of visible light. The UV absorbing compound is typically incorporated into the monomer mixture and is entrapped in the polymer matrix when the monomer mixture is polymerized. Suitable UV absorbing compounds include substituted benzophenones, such as 2-hydroxybenzophenone, and 2-(2-hydroxyphenyl)benzotriazoles. It is preferred to use an UV absorbing compound which is copolymerizable with the monomers and is thereby covalently bound to the polymer matrix. In this way possible leaching of the ultraviolet absorbing compound out of the lens and into the interior of the eye is minimized. Suitable copolymerizable UV absorbing compounds are the substituted 2-hydroxybenzophenones disclosed in U.S. Pat. No. 4,304,895 and the 2-hydroxy-5-acryloxyphenyl-2H-benzotriazoles disclosed in U.S. Pat. No. 4,528,311. The most preferred UV absorbing compound is 2-(3'-methallyl-2'-hydroxy-5' methyl phenyl)benzotriazole, also known as ortho-methallyl TinUVin P ("oMTP").

In a further aspect, the invention provides a method for preparing a transparent, blue-light blocking polymer of the invention. It comprises providing a functionalized bisazo dye and incorporating the dye in a transparent polymer such that it is covalently bound and can not leak out of the polymer matrix. Incorporation of the dye can be achieved by copolymerizing a monomer mixture (e.g. (meth)acrylates) in the presence of at least one functionalized, polymerizable dye. Alternatively, a functionalized dye is reacted with a (co)polymer, such as a silicone polymer.

A method of the invention is characterized by the covalent incorporation of at least one dye of the general Formula V:

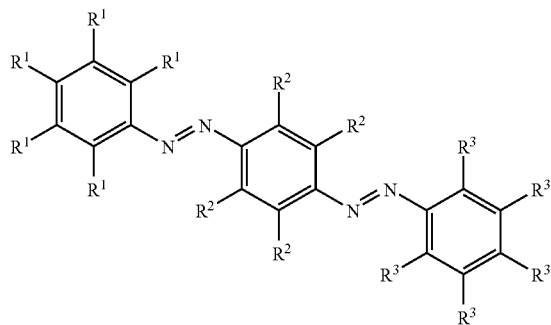

Formula V wherein
each of $R^1$, $R^2$ and $R^3$ is independently selected from hydrogen, sulfonate, nitro, halogen, nitril, phenyl, carboxylate, $-(CH_2)_n-X^1-H$ and $-X^2-(CH_2)_n-CH_3$, wherein $X^1$ is O, NH, $CH_2$ or S; $X^2$ is O, NH, S, $S(=O)_2$, $C(=O)O$; and n is an integer in the range 0 to 20, or wherein two $R^2$ groups together with the C-atoms to which they are bound form a benzene ring;

each of $R^3$ is independently selected from hydrogen, sulfonate, nitro, halogen, nitril, phenyl, carboxylate, $-(CH_2)_n-X^1-H$ and $-X^2-(CH_2)_n-CH_3$, wherein $X^1$ is O, NH, $CH_2$ or S; $X^2$ is O, NH, S, $S(=O)_2$, $C(=O)O$; and n is an integer in the range 0 to 20, provided that at least one $R^3$ is a functional group through which the dye can be covalently bound to the polymer.

Preferred dyes are those having the $R^1$, $R^2$ and $R^3$ groups as defined in the Formula's II, II and IV herein above.

Dyes for use in the present invention can be synthesized according to standard organic synthetic procedures or they may be commercially obtained. Preferably, a bisazo dye is used which is commercially available. If necessary, a linker group can be attached to the dye using standard derivatization techniques. Because various commercially available bisazo dyes contain a hydroxyl group at the third phenyl ring of the general formula, they can be readily derivatized to a dye of Formula V by converting the hydroxyl group to an O-linked linker moiety.

Methods to provide a functionalized dye are known in the art. See for example EP1293541. Of course, it is preferred to use a commercially available bisazo dye which can be readily functionalized to obtain a dye of Formula V. Suitable dyes for use in a method of the invention include Disperse Yellow 7, Disperse Orange 13, Mordant Orange 10 and Mordant Orange 6. Many types of functional groups capable of covalent binding to a polymer have been described in the art. They comprise acryloyl, methacryloyl, allyl, vinyl and isoprenyl groups.

In one embodiment, said functional group is selected from the group consisting of $-(CH_2)_a-CH=CH_2$; $-(CH_2)_b-Z^1-(CH_2)_a-CH=CH_2$; $-(CH_2)_b-C(=O)-Z^1-(CH_2)_a-C(R^5)=CH_2$; $-(CH_2)_b-Z^1-C(=O)-(CH_2)_a-C(R^5)=CH_2$; $-Z^2-(CH_2)_c-Z^1-(CH_2)_a-C(R^5)=CH_2$; $-Z^2-(CH^2)_c-C(=O)-Z^1-(CH_2)_a-C(R^5)=CH_2$; and $-Z^2-(CH^2)_c-Z^1-C(=O)-(CH_2)_a-C(R^5)=CH_2$, wherein a and b are independently selected from an integer from 0 to 10 and wherein c is an integer from 1 to 10; wherein $Z^1$ and $Z^2$ are independently selected from $-O-$ and $-NR^6-$; and wherein $R^5$ and $R^6$ are independently hydrogen, or linear or branched alkyl of $C_1$-$C_{10}$.

In one embodiment, the functional group is an O- or N-linked allyl or vinyl. Examples of functional groups include $-O-CH=CH_2$; $-NH-CH=CH_2$; $-O-C(=O)-C(CH_3)=CH_2$; $-O-C(=O)-CH=CH_2$; $-O-CH_2-CH_2-O-C(=O)-C(CH_3)=CH_2$ and $-O-CH_2-CH_2-O-CH=CH_2$.

Procedures for attaching a functional group to a dye are known in the art. Typically, they involve electrophilic substitution of the alcohol group, leading to ether formation, e.g. the Williamsion Ether Synthesis or ester synthesis with electrophilic derivatives of carboxylic, e.g. acyl chloride or acid anhydride, and sulfonic acids, or by reacting the hydroxy group of the dye with methacrylic anhydride in the presence of a weak base, such as triethylamine, to yield a reactive methacrylic azo-dye.

Methods to prepare a transparent polymer of several types of monomers are also well known in the art. The monomers used for the present invention are not particularly limited so long as they can provide transparent polymer materials. As used herein, the term "transparent" refers to a condition where a material is clear enough not to block the passage of radiant energy, especially light. A "transparent polymer" is a material prepared from one or more types of monomers which polymer is suitable as optical polymer, i.e. a polymer allowing light to pass through and, preferably, allowing to be seen through. Typically, a transparent polymer has a clear surface that is easily seen through with little or no distortion. The monomers referred to above which may be suitably used can be obtained from commercial sources. The polymerization method, conditions, kinds of polymerization initiator and crosslinking agent, the respective amounts thereof and the like can be appropriately selected depending on the desired (co)polymer. Suitable monomers for the manufacture of transparent polymers are known in the art and include alkyl (meth)acrylates, phenylated(meth)acrylates, hydrophilic monomers, silicon-containing monomers and fluorine-containing monomers. In particular, there can be mentioned, for example, linear or branched allyl(meth)acrylates (the expression (meth)acrylate as used herein refers to both an acrylate and a methacrylate) such as methyl methacrylate, butyl(meth)

acrylate and cyclohexyl methacrylate; hydrophilic monomers such as 2-hydroxyethyl methacrylate, glycerol methacrylate, N-vinylpyrrolidone, dimethylacrylamide and methacrylic acid; silicon-containing monomers such as tris(trimethylsiloxy)silylpropyl(meth)acrylate, trimethylsiloxydimethylsilylpropyl(meth)acrylate and bis(trimethylsiloxy)methylsilylpropyl(meth)acrylate; and fluorine-containing monomers such as trifluoroethyl(meth)acrylate, hexafluoroisopropyl (meth)acrylate and perfluorooctylethyloxypropylene(meth) acrylate and the like. Other suitable monomers are vinylalcohol and vinylacetate, polymerisable polyethyleneglycol, polypropylene glycol, perfluoropolyethers and copolymers thereof. The monomers mentioned can be used alone or in any combination.

For the manufacture of a silicone polymer material containing a covalently bound dye, it is preferred to use a silicone compound having hydrosilyl groups which allow for an addition reaction using a catalyst such as platinum. Catalysts using in the addition reaction of dyes to silicone compounds are desirably platinum compounds such as hydrogen chloroplatinate, platinum-divinyltetramethyldisiloxane, and platinum-tetramethyltetravinylcyclosiloxane. Further, a silicone bound to the dye obtained by the above method may provide a silicone elastomer chemically bound to the dye by crosslinking with a silicone having vinyl groups. In accordance with one example of the present invention a blue-light blocking dye is chemically bound to silicone polymer material having hydrosilyl groups and then crosslinked with silicone having vinyl groups. Another method is that the dye is mixed with silicone having hydrosilyl groups or silicone having vinyl groups, and the mixture is mixed with silicone having hydrosilyl groups and silicone having vinyl groups, and then the mixture is cross-linked at the same time as the dye is reacted to the hydrosilyl groups.

Upon mixing of the silicone described above, it is preferable to homogeneously disperse the dye by using an appropriate solvent. As such solvents, acetone, ethanol, chloroform, toluene, tetrahydrofuran, and dichloromethane can be exemplified. The dye is dissolved in the solvent and mixed with silicone. Then, the solvent can be distilled away with an evaporator, and the dye is uniformly dispersed in the silicone.

For a polymer material based on linear or branched alkyl or aryl(meth)acrylate monomers, polymerization can be performed by conventional methods used for the production of copolymers for contact lenses. For example, radical polymerization, photopolymerization and the like can be used. The crosslinking agent are for example, (meth)acrylates of polyalcohol, i.e., di- or more hydric alcohol such as ethylene glycol di(meth)acrylate, diethylene glycol di(meth)acrylate, triethylene glycol di(meth)acrylate and trimethylolpropane tri(meth)acrylate and other compounds including allyl methacrylate, triallyl isocyanurate, vinyl(meth)acrylate and the like can be used. The polymerization initiator used for radical polymerization are for example, those known as common radical generators, for example, peroxides such as lauroyl peroxide, bis(4-t-butylcyclohexyl)peroxydicarbonate and 1,1-bis(t-butylperoxy)3,3,5-trimethylcyclohexane; and azo compounds such as 2,2'-azobisisobutyronitrile, 2,2'-azobis(2, 4-dimethylvaleronitrile), 2,2'-azobis(4-methoxy-2,4-dimethylvaleronitrile) and 2,2'-azobis[2-(2-imidazoline-2-yl)propane]. Bis(4-tert-butylcyclohexyl)peroxydi-carbonate is a preferred peroxide and 2,2'-azobisisobutyronitrile is a preferred azo compound. A suitable amount of the polymerization initiator is in a range of 0.05 to 0.1 part by weight for 100 parts by weight of the monomer mixture. The acrylic monomer mixture is fully stirred so that the components are mixed well, introduced into a mold of rod, cup, or plate shape made of metal, plastic, glass or the like, and sealed. Then, polymerization is performed by raising temperature stepwise in a temperature range of 25 to 150° C. in a temperature controlled bath. It may be preferred as the case may be that the polymerization is performed in a sealed vessel where gases such as oxygen and the like are replaced with an inert gas such as nitrogen or argon.

According to the invention, there is no limitation with respect to the combination of specific dye(s) of formula V and the specific polymer material. However, the skilled person will understand that some dyes are more suitable for covalent attachment to a given polymer than other dyes. This primarily concerns the solubility of the dye(s) in hydrophobic or hydrophilic solvents, monomers or polymers.

Preferred dyes for incorporation in silicone polymers or acrylate polymers are those which have a good solubility in organic solvents like chloroform and ethylene glycol monomethyl ether (EGME). Examples of dyes which, in solution are well miscible with silicone resin or acrylates include Disperse Yellow 7 which has a solubility in EGME of 80 mg/ml.

Conversely, for incorporation into hydrophilic polymers, such as hydrophilic acrylates, anionic dyes are preferred having a good solubility in aqueous solvents. For instance, the solubility of Mordant Orange 6 and 10 in water is 40 mg/ml.

Another factor which may affect the compatibility of dye and polymer resides in the substituent(s) present on the dye molecule. Amino substituents are less favourable if the dye is to be incorporated to a silicone polymer, since they may interfere with the platinum catalyst used for cross-linking the silicone polymer.

Based on the above together with his general knowledge, a person skilled in the art will be able to select a suitable combination of dye and polymer with undue burden.

The invention furthermore provides the use of a polymer material of the invention, in particular for the manufacture of a lens. A functionalized dye of formula V is also provided. Such a dye, optionally in combination with additional compounds capable of absorbing light of predetermined wavelengths in the UV or in the visible light spectrum (400-700 nm), is advantageously incorporated in a number of transparent polymer materials in a variety of applications where it is desirable to block or minimize the transmission of light with a wavelength of about 400-550 nm. Such applications may include, for example, contact lenses, eye glasses and sunglasses. Lenses for eyes, obtained by bonding a dye of general Formula V and another UV absorbing agent to silicone or by copolymerization of the dye with a monomer constituting lenses, can shut off the greater part of incident blue-to-violet light to the eyes, thereby reducing the bad influence of lower blue light upon eyes.

The invention furthermore provides an ophthalmic lens comprising a transparent polymer material containing at least one covalently bound dye of the general formula I. The term "ophthalmic lens", as used herein, refers to lenses which are placed in intimate contact with the eye or tear fluid, such as contact lenses for vision correction (e.g., spherical, toric, bifocal), contact lenses for modification of eye color, ophthalmic drug delivery devices, ocular tissue protective devices (e.g., ophthalmic healing promoting lenses), intraocular lenses, and the like.

Due to the unique absorption properties of the bisazo dyes disclosed herein, a lens according to the invention is capable of blocking at least 20-30% of the visible light in the 480-500 nm region. Furthermore, it displays a significant absorption at wavelengths above 500 nm. For example, a transmission of only 75% was observed at 550 nm, which is a good approximation of the reported 65-70% transmission of an aged human crystalline lens. In contrast, the prior art lens materials show 85% or more transmission at 550 nm.

As an additional advantage, an optical lens made of a polymer of the invention displays less chromatic aberrations as compared to lenses described in the prior art. Chromatic aberrations are wavelength-dependent artefacts that occur because the refractive index of every optical lens formulation varies with wavelength. When white light passes through a simple or complex lens system, the component wavelengths are refracted according to their frequency. In most lenses, the refractive index is greater for shorter (blue) wavelengths and changes at a more rapid rate as the wavelength is decreased. Blue light is refracted to the greatest extent followed by green and red light, a phenomenon commonly referred to as dispersion. The inability of a lens to bring all of the colours into a common focus results in a slightly different image size and focal point for each predominant wavelength group. This leads to colored fringes surrounding the image. Thanks to the close approximation of the natural transmission spectrum in the visible light spectrum, the lens of the invention suffers less from chromatic aberrations. Accordingly, the quality of vision, in particular the sharpness of the retinal image, when using a lens of the invention is less compromised.

A particularly preferred ophthalmic lens is an intraocular lens (IOL). As such, one embodiment of the invention is an IOL containing a dye of the general formula I, optionally in combination with one or more additional dyes, for example a UV-absorbing compound blocking rays up to 400 nm and/or a second dye which blocks in the region above 400 nm. The term "intraocular lens" refers to an artificial lens that may be surgically implanted in a patient's eye after removing the eye's natural lens, usually replacing the existing crystalline lens because it has been clouded over by a cataract. An IOL usually consists of a plastic lens with plastic side struts called haptics to hold the lens in place within the capsular bag. Like a contact lens, it has a built-in refractive power tailored specifically to the patient's visual condition. There are numerous styles of IOLs, including foldable IOLs and multifocal IOLs.

In one exemplary embodiment, the IOL of present invention is a soft, foldable, silicone IOL having incorporated therein at least one dye of formula I. However, it is understood that while the present invention will be described most extensively using a soft IOL as an example (see Examples 1 and 2 below), it is not limited to soft silicone IOLs. For example, the present invention is equally suitable for soft acrylic IOLs, acrylic-silicone hybrid IOLs and hard PMMA IOLs. Persons skilled in the art will readily understand to easily adapt the present teachings for use with other IOL structural polymers.

Also provided is a method for the manufacture of an ophthalmic lens of the invention, comprising a transparent polymer material of the invention and furthermore comprising shaping said polymer material into a lens shape. In one embodiment, said shaping is performed by injection moulding and crosslinking said polymer material into a lens shape mold. In case of an IOL, the manufacture process typically also comprises the attachment of haptics. Methods to prepare lenses, including IOLs, from transparent polymer material are well known in the art (U.S. Pat. No. 5,444,106, WO9631792, U.S. Pat. No. 4,120,570). In one embodiment, it comprises the manufacture of the desired polymer in the shape of a rod or plate shape material, which material can be cut into button shape blanks and made into a lens shape by cutting and polishing. Alternatively, by pouring the above monomer mixture into a lens shape mold having a desired curvature and polymerizing it, the monomer mixture may be directly made into a lens shape.

In a specific aspect, the invention provides an IOL comprising a transparent polymer material of the invention, wherein the transparent polymer material containing the dye of formula I is present in a limited region of the lens. Specific reference is made to WO 2005/066694 disclosing an IOL wherein a light absorbing dye is localized to a specific part of the lens, preferably the center portion. Advantages of this configuration are that it affords the retina maximum protection in high intensity lighting condition where protection is needed most, while permitting a fuller spectrum of light to reach the retina in subdued, or low light conditions. Furthermore, the light absorbing dye may be isolated within the IOL interior such that the dye itself does not contact either the eye's anatomical structures or physiological fluids.

The invention is exemplified by the Examples herein below.

BRIEF DESCRIPTIONS OF DRAWINGS

FIG. 1: Transmission spectrum of a transparent polymer of the invention containing a bisazo dye of Formula I ("Ophtec-orange") and a conventional UV-absorbing compound. Also shown are the spectra of two known yellow "blue-light absorbing" IOLs (AcrySof Natural IOL from Alcon and Hoya IOL (HOYA YA-60BB) and the reported transmission spectrum of an aged human lens (Boethner. E. A. and Wolter. J. R., "Transmission of the Ocular Media", Investigative Ophthalmology, Vol. 776-783, 1962).

Figure 2:
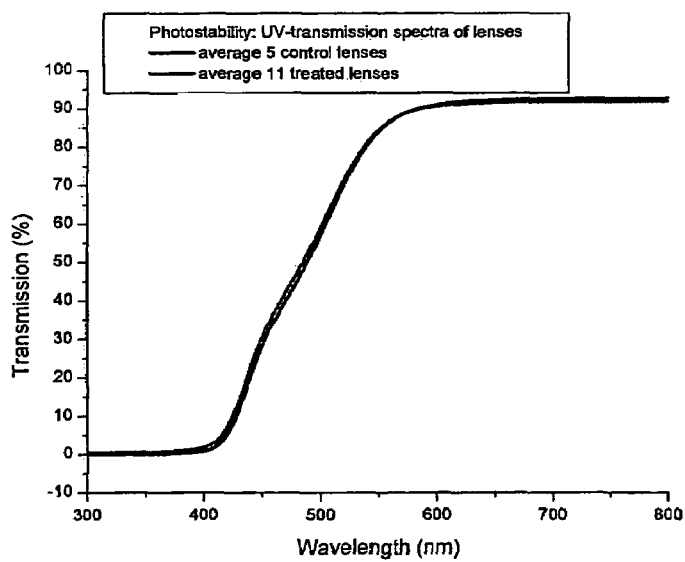

FIG. 2: UV-transmission curves of treated and non-treated (control) lenses demonstrating the photostability of dye-containing polymer material of the invention. For details see Example 3.

Figure 3:
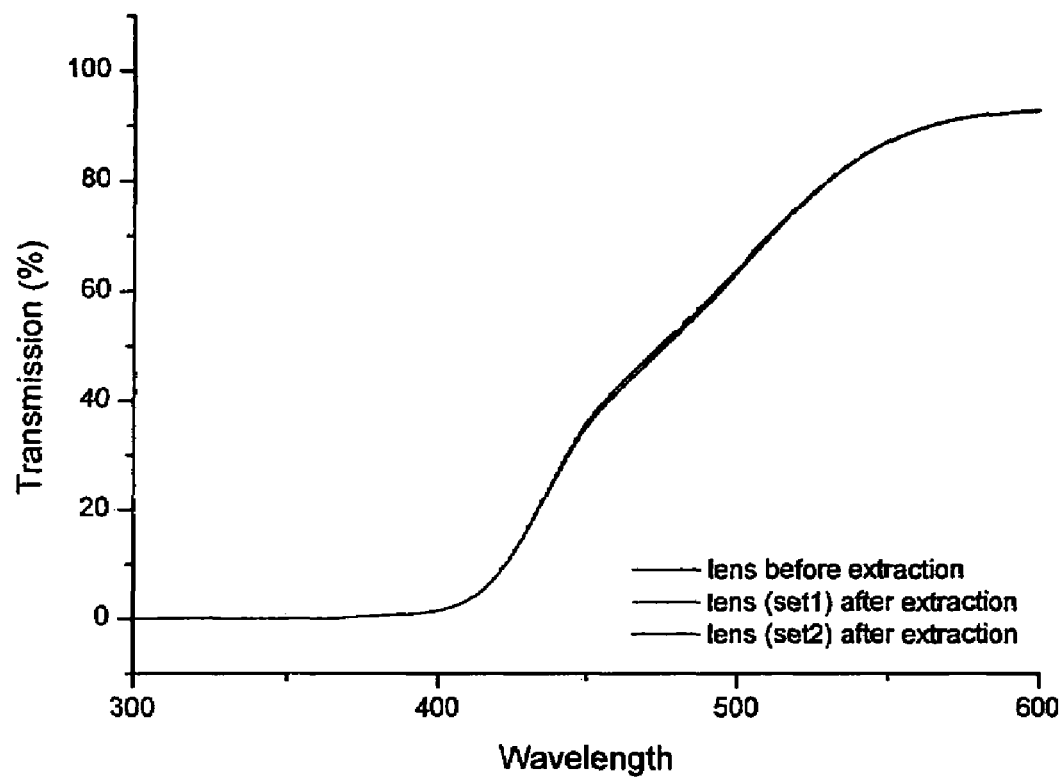

FIG. 3: UV-transmission curves of extracted and non-extracted (control) lenses demonstrating that the dye was covalently incorporated in the polymer material. For details see Example 4.

EXPERIMENTAL SECTION

Example 1

Functionalization of Disperse Yellow 7

In this example, the commercially available dye Disperse Yellow 7 is functionalized at its free hydroxyl with an allyl linker moiety to allow for covalent attachment of the dye to a polymer, in this case a silicone polymer.

Materials:
　Disperse Yellow 7, supplier: Sigma Aldrich
　Allyl bromide, suppliers: Acros/Boom BV/Fisher-Emergo
　Potassium carbonate ($K_2CO_3$)
　Sodium chloride
　Diethyl ether
　Magnesium sulfate ($MgSO_4$)
　Acetone p.a.
　Hexane p.a.

Procedure:
　250 ml acetone p.a. was added to 5 g of Disperse Yellow 7 and 3.3 g of $K_2CO_3$. The mixture was stirred at room temperature under nitrogen atmosphere and then heated to 68° C. under reflux for two hours. After cooling down to room temperature, 2.87 g of allyl bromide was added dropwise. The temperature was increased again to 68° C. and the mixture was allowed to react under stirring and refluxing of acetone overnight. Demineralized water (about 400 ml) was added under stirring. Next, 30 g of NaCl p.a. was added. De mixture was transferred to a separating funnel of 3000 ml and shaken with 200 ml diethyl ether. The water/acetone layer was separated from the layer of diethylether. The mixture was shaken and separated with 100 ml of water for two more times. The ether layer was dried over 40 g of $MgSO_4$, filtered and evaporated. The product was dried under vacuum and dissolved in aceton p.a. Hexane p.a. was added until the solution became opaque. Crystals of the purified product were formed overnight in the freezer. The crystals were collected trough filtration and subsequently dried in a vacuum exsiccator.

Example 2

Covalent Attachment of Functionalized Disperse Yellow 7 to Silicone Co-Polymer and Preparation of Intraocular Lens (IOL)

In this example, an IOL is prepared from a silicone material comprising the functionalized dye of Example 1. The polymer is prepared using the commercially available two component system Silicone Med 6820 from NuSil Technology.

Materials:
  Silicone Med 6820 component A (NuSil Technology)
  Silicone Med 6820 component B (NuSil Technology)
  Functionalized Disperse Yellow 7 (see Example 1)
  Functionalized 2,4 dihydroxybenzophenone UV-Blokker (functionalization comparable to the functionalization of Disperse Yellow 7, example 1)
  Dichloromethane Procedure:
  500 g of component A, 1.9 g functionalized UV blocker and 0.1 g functionalized Disperse Yellow 7 were transferred to a reaction vessel. The mixture was dissolved in 1 liter dichloromethane and stirred for one hour. Thereafter, the dichloromethane was evaporated using a rotation evaporator and the silicone was simultaneously degassed. The procedure was repeated for component B Component A and component B were mixed (1:1 volume ratio) in a static mixer. The mixture was injected into a IOL-mould and cured at 120° C. for 10 minutes. Subsequently, the polymer material was post-cured at 150° C. for 2 hours. After moulding the IOL's were polished, extracted and cleaned. The resulting IOLs contain 0.02 wt % of the functionalized dye and 0.38 wt % of the UV-blocker.

Example 3

Photostability Test and Cytotoxicity Test of the Dye-Containing Intraocular Lens (IOL)

Procedure
  The IOL containing the covalently bound Disperse Yellow 7 was tested for its susceptibility to photochemical degradation. In this study 45 lenses were immersed in 2 ml saline solution and exposed to UV-light (300-400 nm) with a dose equivalent to 20 years of daylight. After exposure an established in vitro cytotoxicity test MEM Elution Test; for reference see standard 'Ophtalmic implants—intraocular lenses—Part 5: Biocompatibility ISO 11979-5: 1999, modified') was performed on the saline solution. The UV-transmission curves of the lenses were studied before an after exposure.

Results Cytotoxicity (MEM Elution Test)
  No biological reactivity (Grade 0) was observed in the L929 mammalian cells at 48 hours, post exposure to the article extract and the treated blanc saline. The observed cellular response obtained from the positive control extract (Grade 4) and the negative control extract (Grade 0) confirmed the suitability of the test system. These results demonstrate that the blue-light blocking IOL of the invention is considered non-cytotoxic and meets the requirements of the Elution test.

Results UV-Transmission Curves of the Dye-Containing IOL's
  The UV-Transmission curves of the UV-irradiated and control lenses were measured. The results are given in FIG. 2. The absorption characteristic of the orange IOL of the invention is preserved after the treatment equivalent to 20 years of daylight. A decrease in transmission at 500 nm of only 3% is observed. This corresponds to a loss of activity of only 5% of the Disperse Yellow 7 molecules in the material.

Example 4

Exhaustive Extraction Test of the Dye-Containing IOL's

Procedure
  To demonstrate that the dye was efficiently incorporated covalently in the polymer material, the IOL's were extracted with toluene by using a soxhlet apparatus. Toluene is a good solvent for Disperse Yellow 7 and the crosslinked silicone material swells considerably in toluene. The extraction was performed in duplicate using sample sets of 20 lenses each. Five lenses per sample set were subjected to UV/VIS transmission spectroscopy before extraction to serve as controls.
  FIG. 3 shows the UV-Vis transmission spectroscopy results of the extracted lenses as compared to the control lenses. The UV-transmission of the lenses at 475 nm before and after extraction was 50%. The overlapping spectra show that the absorption characteristic of the lenses is preserved during extraction, indicating that Disperse Yellow 7 is covalently bound to the silicon material.

Example 5

Synthesis of Functionalized Disperse Orange 13

Azo Coupling of 1-Naphthyl Red Hydrochloride to 2-phenoxyethanol (Synthesis of Compound I)

Into a 100 ml beaker is added 200 ml water and 14.2 (100 mmol) of sodium phosphate, dibasic ($Na_2HPO_4$) followed by the addition of 6N HCl solution to adjust the reaction solution to pH 2. After the phosphate buffer salt is completely dissolved, 14.426 g (50.84 mmol) of 1-naphthyl red hydrochloride (Sigma Aldrich) is added to the solution. Ice is added to the reaction solution to cool it down to 0° C.
  Into a separate beaker, 3.5151 g (50.94 mmol) of sodium nitrite, $NaNO_2$, is dissolved in 20 ml of water. Ice is added to cool the solution. The sodium nitrile solution is added dropwise with constant stirring to the reaction solution while constantly monitoring the pH of the reaction. The pH of the reaction is maintained to about 1.9 to 2.2 by addition of 6N HCl. After the addition of sodium nitrite solution is completed, more ice is added to the reaction to keep the temperature at 0° C.-10° C. and the reaction is stirred for about 15 minutes.

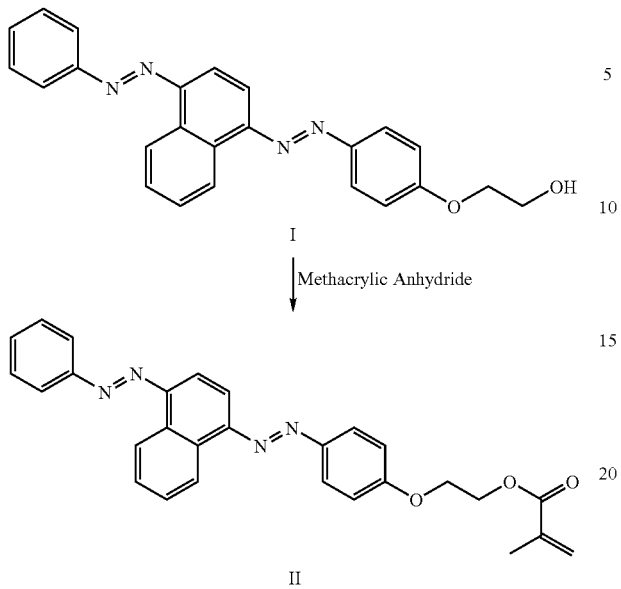

I

↓ Methacrylic Anhydride

II

Into another beaker is placed 6.9743 (50.48 mmol) 2-phenoxyethanol (Sigma Aldrich), 100 ml of water, and enough 6N HCl is added to dissolve the solid. The 2-phenoxyethanol solution is added dropwise into the stirring reaction solution which was kept at 0° C.-10° C. by periodic addition of ice. After the addition is completed the solution is stirred for about an hour and warmed up to 10° C. then 50% w/v and 2N NaOH solutions were added to the reaction solution to pH 6.9. The solid was filtered of and washed with water. The solid obtained from the reaction is recrystallized and dried.

Functionalisation of Compound I (Synthesis of Compound II)

Into a 100 ml round bottomed flask is placed 5.011 mmol of compound I and 25 ml THF. Subsequently 1.5549 g (10.086 mmol) methacrylic anhydride (MAA) is added. After about 4 hours 1.0452 g (10.329 mmol) of triethylamine is added dropwise to the reaction solution. The reaction is stirred for 2 days and then another aliquot of 4.1877 g (41.385 mmol) of triethylamine is added to the reaction. The product is purified by column chromatography.

Example 6

Covalent Attachment of Functionalized Disperse Orange 13 to Methacrylate Polymer and IOL Preparation 0.1 gram 2,2-azobis(2,4-dimethylvaleronitrile) as a polymerization initiator is mixed with 10 gram 2-phenoxyethyl acrylate, 80 gram 2-hydroxyethyl methacrylate, 10 gram methyl methacrylate, 0.02 gram functionalized Disperse Orange 13 (see Example 5) and 0.38 gram acrylate functionalised UV-blocker. The mixture is poured in a glass tube and the tube is put in a water bath to polymerize it by maintaining at 35° C. for about 40 hours and heating at 50° C. for 8 hours. Subsequently, the above-mentioned tube is transferred to a circulating drier, and heated from 50° C. to 120° C. at a rate of 10° C. per 1.5 hours. It is maintained at 130° C. for 3 hours and allowed to stand to cool to room temperature to obtain a cylindrical transparent copolymer comprising the dye. The material is cut into buttons. IOL's are prepared from the buttons by machining and subsequently polishing according to standard procedures.

The invention claimed is:

1. Transparent polymer material containing at least one covalently attached dye, said dye having the general formula I:

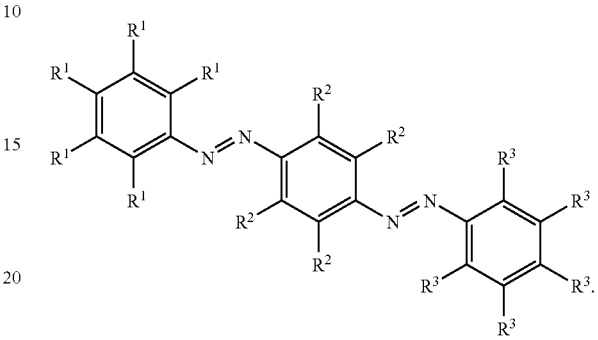

wherein
each of $R^1$, $R^2$ and $R^3$ is independently selected from hydrogen, sulfonate, nitro, halogen, nitril, phenyl, carboxylate, —$(CH_2)_n$—$X^1$—H and —$X^2$—$(CH_2)_n$—$CH_3$, wherein $X^1$ is O, NH, $CH_2$ or S; $X^2$ is O, NH, S, S($=$O)$_2$, C($=$O)O; and n is an integer in the range 0 to 20; or wherein two groups together with the C-atoms to which they are bound form a benzene ring;
provided that at least one $R^3$ is a linker moiety L through which the dye is covalently bound to the polymer.

2. Transparent polymer material according to claim 1, wherein at least one $R^3$ at the meta-position relative to the azo-group is a linear or branched $C_1$-$C_{20}$ alkyl.

3. Transparent polymer material according to claim 1 or 2, wherein $R^1$ at the para-position is a sulfonate and wherein at least one $R^3$ at the meta-position is a carboxylate.

4. Transparent polymer material according to claim 1 or 2, wherein two $R^2$ groups together with the C-atoms to which they are bound form a benzene ring.

5. Transparent polymer material according to claim 1 or 2, wherein said linker moiety is positioned at the para-position relative to the azo-group.

6. Transparent polymer material according to claim 1 or 2, wherein said linker moiety L is selected from the group consisting of —$(CH_2)_a$—$CH_2$—$CH_2$—; —$(CH_2)_b$—$Z^1$—$(CH_2)_a$—$CH_2CH_2$—; —$(CH_2)_b$—C($=$O)—$Z^1$—$(CH_2)_a$—CH($R^5$)—$CH_2$—; —$(CH_2)_b$—$Z^1$—C($=$O)—$(CH_2)_a$—CH($R^5$)—$CH_2$—; —$Z^2$—$(CH_2)_c$—$Z^1$—$(CH_2)_a$—CH($R^5$)—$CH_2$—; —$Z^2$—$(CH_2)_c$—C($=$O)—$Z^1$—$(CH_2)_a$—CH($R^5$)—$CH_2$— and —$Z^2$—$(CH_2)_c$—$Z^1$—C($=$O)—$(CH_2)_a$—CH($R^5$)—$CH_2$—;
wherein a and b are independently selected from an integer from 0 to 10 and wherein c is an integer from 1 to 10; wherein $Z^1$ and $Z^2$ are independently selected from —O— and —$NR^6$—; and wherein $R^5$ and $R^6$ are independently hydrogen, or linear or branched alkyl of $C_1$-$C_{10}$.

7. Transparent polymer material according to claim 1 or 2, wherein the total amount of the dye of general formula I is less than 5 wt.

8. Transparent polymer material according to claim 1 or 2, comprising an additional dye capable of absorbing light within the visible light spectrum.

9. Transparent polymer material according to claim 1, furthermore comprising an ultraviolet absorbing compound.

10. Transparent polymer material according to claim 1 or 2, wherein said material comprises one or more monomers selected from the group consisting of linear or branched (meth)acrylates, hydrophilic monomers, silicon-containing monomers and fluorine-containing monomers.

11. Method for preparing a polymer material according to claim 1, comprising the steps of:
   a. providing a functionalized dye, and
   b. incorporating the functionalized dye in the polymer, wherein said incorporating comprises copolymerizing a monomer mixture comprising the functionalized dye or reacting the functionalized dye with a (co)polymer, and wherein said functionalized dye has the general formula V:

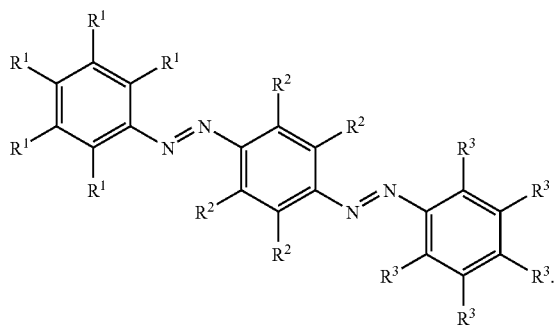

wherein
   each of $R^1$, $R^2$ and $R^3$ is independently selected from hydrogen, sulfonate, nitro, halogen, nitril, phenyl, carboxylate, $-(CH_2)_n-X^1-H$ and $-X^2-(CH_2)_n-CH_3$, wherein $X^1$ is O, NH, $CH_2$ or $X^2$ is O, NH, S, $S(=O)_2$, $C(=O)O$; and n is an integer in the range 0 to 20; or wherein two $R^2$ groups together with the C-atoms to which they are bound form a benzene ring;

provided that at least one $R^1$ is a functional group through which the dye can be covalently bound to the polymer.

12. Method according to claim 11, wherein said functional group is positioned at the para-position relative to the azo-group, and wherein said functional group is selected from the group consisting of $-(CH_2)_a-CH=CH_2$; $-(CH_2)_b-Z^1-(CH_2)_a-CH=CH_2$; $-(CH_2)_b-C(=O)-Z^1-(CH_2)_a-C(R^5)=CH_2$; $-(CH_2)_b-Z^1-C(=O)-(CH_2)_a-C(R^5)=CH_2$; $-Z^2-(CH_2)_c-Z^1-(CH_2)_a-C(R^5)=CH_2$; $-Z^2-(CH_2)_c-C(=O)-Z^1-(CH_2)_a-C(R^5)=CH_2$ and $-Z^2-(CH_2)_c-Z^1-C(=O)-(CH_2)_a-C(R^5)=CH_2$,
   wherein a and b are independently selected from an integer from 0 to 10 and wherein c is an integer from 1 to 10; wherein $Z^1$ and $Z^2$ are independently selected from $-O-$ and $-NR^6-$; and wherein $R^5$ and $R^6$ are independently hydrogen, or linear or branched alkyl of $C_1$-$C_{10}$.

13. A method for manufacturing a lens, comprising incorporating a transparent polymer material according to claim 1 or 2 into a lens.

14. Ophthalmic lens comprising a transparent polymer material according to claim 1.

15. A method for the manufacture of an ophthalmic lens, comprising a polymer material according to claim 1 or 2, comprising the steps of:
   a. providing a functionalized dye, and
   b. incorporating the functionalized dye in the polymer, wherein said incorporating comprises copolymerizing a monomer mixture comprising the functionalized dye or reacting the functionalized dye with a (co)polymer, and wherein said functionalized dye has the general formula V:

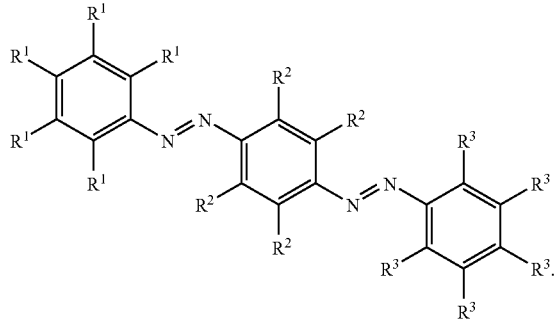

wherein
   each of $R^1$, $R^2$ and $R^3$ is independently selected from hydrogen, sulfonate, nitro, halogen, nitril, phenyl, carboxylate, $-(CH_2)_n-X^1-H$ and $-X^2-(CH_2)_n-CH_3$, wherein $X^1$ is O, NH, $CH_2$ or X is O, NH, S, $S(=O)_2$, $C(=O)O$; and n is an integer in the range 0 to 20; or wherein two $R^2$ groups together with the C-atoms to which they are bound form a benzene ring;

provided that at least one $R^3$ is a functional group through which the dye can be covalently bound to the polymer; and c. shaping said polymer material into a lens.

16. Ophthalmic lens comprising a transparent polymer material according to claim 2.

17. Lens of claim 14 or 16, said lens being a foldable intraocular lens (IOL).

18. Transparent polymer material according to claim 2, wherein the linear or branched $C_1$-$C_{20}$ alkyl is a $C_1$-$C_4$ alkyl.

19. Transparent polymer material according to claim 18, wherein the $C_1$-$C_4$ alkyl is a methylene.

20. Transparent polymer material according to claim 1 or 2, wherein the total amount of the dye of general formula I is less than 1 wt %.

21. Transparent polymer material according to claim 2, furthermore comprising an ultraviolet absorbing compound.

22. Transparent polymer material according to claim 9 or 21, wherein the ultraviolet absorbing compound, is a benzophenone or benzotriazole.

23. Transparent polymer material according to claim 1 or 2, wherein the polymer comprises silicon-containing monomers.

24. Method according to claim 15, wherein said functional group is positioned at a the para-position relative to the azo-group, wherein said functional group is selected from the group consisting of $-(CH_2)_a-CH=CH_2$; $-(CH_2)_b-Z^1-(CH_2)_a-CH=CH_2$; $-(CH_2)_b-C(=O)-Z^1-(CH_2)_a-C(R^5)=CH_2$; $-(CH_2)_b-Z^1-C(=O)-(CH_2)_a-C(R^5)=CH_2$; $-Z^2-(CH_2)_c-Z^1-(CH_2)_a-C(R^5)=CH_2$; $-Z^2-(CH_2)_c-C(=O)-Z^1-(CH_2)_a-C(R^5)=CH_2$ and $-Z^2-(CH_2)_c-Z^1-C(=O)-(CH_2)_a-C(R^5)=CH_2$,
   wherein a and b are independently selected from an integer from 0 to 10 and wherein c is an integer from 1 to 10; wherein $Z^1$ and $Z^2$ are independently selected from $-O-$ and $-NR^6-$; and wherein $R^5$ and $R^6$ are independently hydrogen, or linear or branched alkyl of $C_1$-$C_{10}$.

* * * * *